United States Patent [19]
Castillo et al.

[11] 4,050,453
[45] Sept. 27, 1977

[54] RADIOTRANSPARENT ELECTRODE

[75] Inventors: Horace T. Castillo; Henry J. L. Marriott, both of St. Petersburg, Fla.

[73] Assignee: Concept, Inc., Clearwater, Fla.

[21] Appl. No.: 654,911

[22] Filed: Feb. 3, 1976

[51] Int. Cl.² ............................................... A61B 5/04
[52] U.S. Cl. ............................ 128/2.06 E; 128/417; 128/DIG. 4
[58] Field of Search ............. 128/2.06 E, 2.1 E, 404, 128/410, 411, 416, 417, 418, DIG. 4

[56] References Cited

U.S. PATENT DOCUMENTS

| | | | |
|---|---|---|---|
| 3,151,619 | 10/1964 | Sullivan | 128/417 |
| 3,170,459 | 2/1965 | Phipps et al. | 128/2.06 E |
| 3,547,104 | 12/1970 | Buffington | 128/2.06 E |
| 3,572,323 | 3/1971 | Yuan | 128/2.06 E |
| 3,587,565 | 6/1971 | Tatoian | 128/2.06 E |
| 3,669,110 | 6/1972 | Low | 128/2.1 E |
| 3,828,766 | 8/1974 | Krasnow | 128/2.1 E |
| 3,865,099 | 2/1975 | Robichaud | 128/2.06 E |
| 3,868,946 | 3/1975 | Hurley | 128/2.1 E |

OTHER PUBLICATIONS

Schaudinischky et al., "The Shape Conforming Electrode," Med. & Biol. Eng., vol. 7, pp. 341-343, 1969.
Leask et al., "A Multi-Poled Printed Circuit Electrode," Lancet, #7342, May 16, 1964, p. 1082.

Primary Examiner—John D. Yasko
Assistant Examiner—Lee S. Cohen
Attorney, Agent, or Firm—Gipple & Hale

[57] ABSTRACT

A disposable radiotransparent electrode comprising a foam container provided with an adhesive surface, a layered conductive structure composed of a mylar plastic base and a gold metallic layer mounted in a well defined in the foam container, an insulated wire connected to the metal film layer with the other end of the wire secured to a connecting pin, a mounting board defining a well mounted to the adhesive surface, a sponge placed in the well positioned adjacent to the layered conductive structure when the mounting board is mounted to the adhesive surface, and electrode gel placed in the mounting board well.

7 Claims, 2 Drawing Figures

RADIOTRANSPARENT ELECTRODE

BACKGROUND OF THE INVENTION

The invention relates broadly to electrode assemblies which are designed for application to the human body as a component of an electrocardiograph apparatus and more specifically to a disposable radiotransparent electrode which can be used as a component of a radiotransparent electrode assembly.

In the X-ray examination of the heart during cardiac catheterization to detect disease, it is conventional to simultaneously record the electrical activity of the heart. This is presently done by attaching large metal electrodes to the arms and legs of the patient near the hands and feet. This attachment retricts movement by the patient. Another problem is that the arm and leg muscles generate electrical potentials that obscure the heart signal and movement of the arms and legs causing the electrodes to generate additional interfering voltages. These deficiencies are usually overcome in practice by mounting the electrodes directly on the chest but conventional electrodes currently being used interfere with and obscure important details in the X-ray image. Thus it can be seen that improved electrocardiographic (ECG) recordings during X-ray examination of the heart could be provided if electrodes were available that did not interfere with the X-ray image. Such electrodes when applied as close to the heart as possible provide a better signal to noise ratio and detect improved waveform details due to the higher current densities that exist in the cardiac area as compared to the limb regions.

Thus the present invention deals with ECG electrodes that are substantially invisible in X-ray images, have excellent electrical properties for electrocardiograph recording and do not interfere with fluoroscopic or X-ray procedures.

DESCRIPTION OF THE PRIOR ART

Disclosure of radiotransparent electrode has already been discussed in the prior art by the present inventors in the Journal of Electrocardiology and Journal of the Association for the Advancement of Medical Instrumentation. In the Journal of The Association for the Advancement of Medical Instrumentation Vol. 8 No. 2, March–April, 1974 the present inventors mentioned the need and use of radiotransparent electrodes. The design set forth in this publication for these radiotransparent electrodes resulted in a ring-like foam rubber container 3 millimeters thick with a 25 centimeter length of size 8 French vinyl feeding tube terminating in a foam well with an opening of 15 millimeters that interfaced with a silver disc. The electrodes added approximately 5000 ohms to the circuit compared with clinical electrodes and were invisible under an image intensifier. Furthermore, such electrodes were routinely used during 25 cardiac catheterizations and provided excellent data on ECG precordial lead waveforms.

In the Journal of Electrocardiology Volume 7 (3) pages 281–282, 1974 the present inventors disclosed a radiotransparent electrode for recording precordial leads during a routine cardiac catheterization. In the electrode shown in this article a 35 millimeter latex callous pad with a 15 millimeter diameter opening interfaces with the patient at the precordial location. A plastic tube 25 centimeters long with an inner diameter of 1.5 millimeters is connected to another latex foam container having a 2 centimeter silver disc at the bottom. The complete assembly is filled with an electrode paste.

In addition, conductive gels have been used for effecting a more efficient conductive connection between the skin surface of the patient and the electrode. In this connection some difficulty has occurred as the gel is sometimes wiped off the electrode during application of the electrode to the patient. The present invention overcomes this difficulty by retaining the gel on the electrode area through the utilization of an sponge having a low mass which conducts through the electrode gel and through its simple construction which keeps the electrode gel in place within the device.

SUMMARY OF THE INVENTION

The present invention generally pertains to electrodes and more specifically to a radiotransparent ECG electrode that is invisible on X-ray images and which has excellent electrical properties. In the electrode a thin film of gold is deposited on a plastic backing and the composite disc is connected to a wire connection. The electrode is mounted on a foam mounting pad. Thus the invention provides an inexpensive single use disposable electrode including electrode gel which provides a uniform area of contact and can be manufactured economically. This construction saves time and the waste of materials as well as providing a safe reliable instrument for diagnostic use.

Although the invention will be set forth in the claims the invention itself and the manner in which it may be made and used, may be better understood by referring to the following description taken in connection with the accompanying drawings forming a part thereof in which like reference numerals refer to like parts throughout the several views and in which:

DETAILED DESCRIPTION OF THE INVENTION

Figure 1:
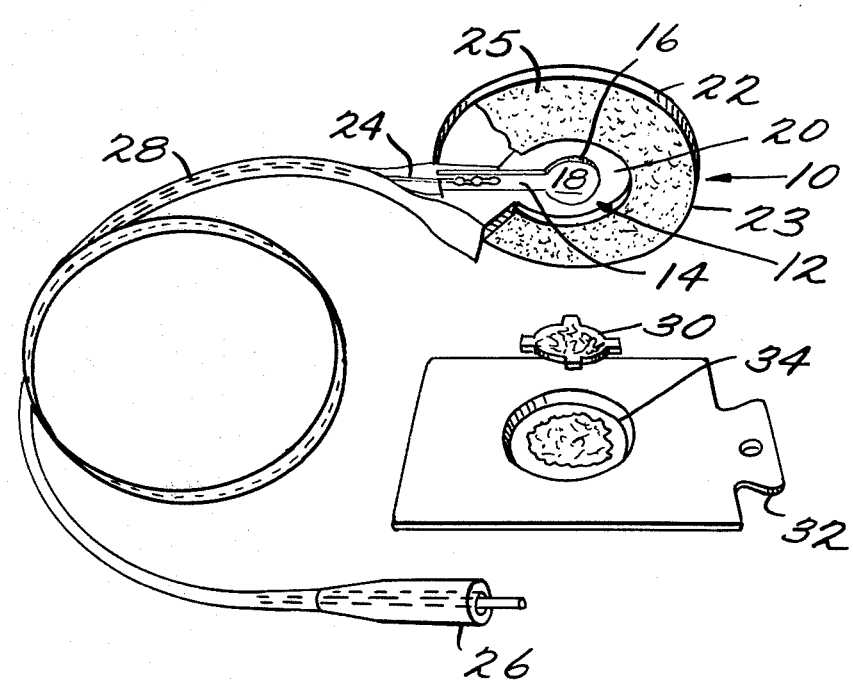
FIG. 1 is an exploded perspective view of the radiotransparent electrode partially in section showing the component parts thereof.

The radiotransparent electrode 10 as shown in FIG. 1 generally comprises a durable composite electrode assembly mounted in a well cut in a latex foam container 22. The electrode 10 is constructed with a disc shaped conductor section 12 approximately 12 millimeters in diameter and an integral tang or shank portion 14 extending therefrom.

The electrode assembly preferably comprises a thin flexible plastic base layer 16 which preferably is mylar 2 mils in thickness upon which is deposited a top layer in the form of a thin film of gold 18, approximately 3000 angstroms thick. The gold is vacuum deposited on the mylar base 16 to arrive at the desired uniform convering. The mylar base layer 16 can alternatively be constructed of paper or other similar flexible selectively insulated material. The disc and tang 14 which is provided for a wire connection is mounted in a shallow circular well 20 cut in the latex foam container 22. The foam container 22 is preferably circular in shape and has a diameter of 50 millimeters and a thickness of 5 millimeters. A single copper wire 24 is soldered to the top of the tang 14. The wire is preferably a number 36 AWG single strand copper wire about 18 inches long and flexible. The other end of the wire 24 terminates in a connector assembly 26 which is compatible with most ECG recording cables. The wire 24 is contained in reinforced plastic tape 28 so as to provide an excellent electrical conductor with strong mechanical properties. The tape is preferably two layers of a strapping tape affixed together to cover the wire between the two layers of tape so that an insulated connector is formed.

The gold layered electrode assembly 12 sits in the well 20 and engages a sponge 30 containing a suitable conductive gel both of which are carried by mounting board 32. The container mounting surface 23 is provided with an adhesive 25 so that the container can be mounted to the mounting board 32. The mounting board 32 is provided with a well 34 which receives the sponge 30 and the electrode gel. The mounting board can be constructed of plastic, paper or cardboard depending upon the construction desired. Thus the electrode can be used one time and disposed of after use.

In the invention the thin layer of gold metal film provides a unique feature in that it is provided specifically to not be observed in X-ray images and to be electronically stable. The copper wire is also selected to be adequate electronically but not to interfere with X-ray procedures. Conventional electrode metal and wire thicknesses currently being used would interfere with such X-ray procedures, and the X-ray transparency of the claimed electrode as compared to the interfering shadow caused by conventional electrodes has been demonstrated.

Figure 2:
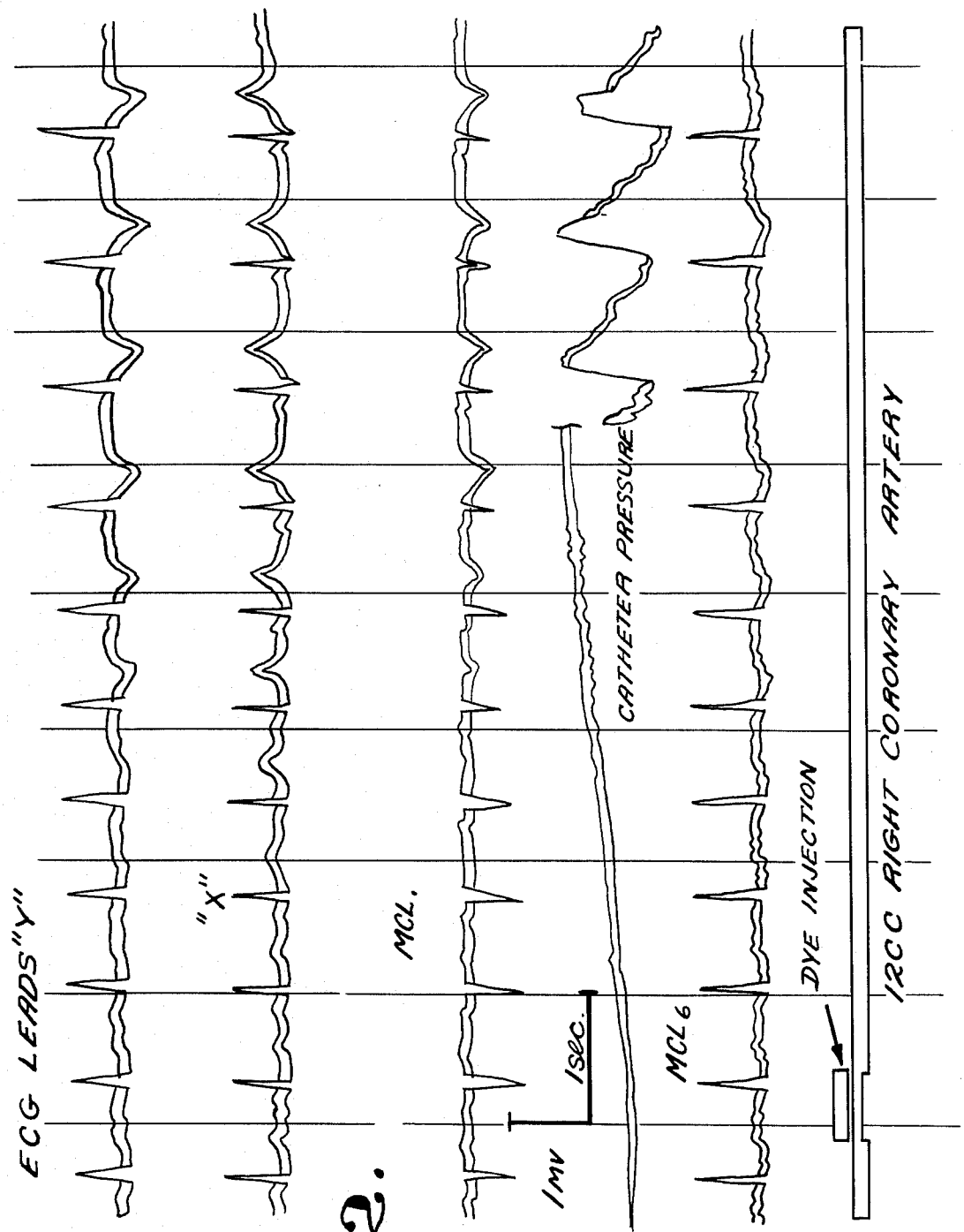
FIG. 2 is a sample of ECG data recorded with the radiotransparent electrode in FIG. 1 during catheterization procedures to detect coronary artery disease.

A sample of the ECG wave forms recorded from the preferred electrode during cardiac catheterization is provided by FIG. 2.

The electrodes as disclosed are X-ray invisible and facilitate improved ECG recordings during cardiac catheterization or any X-ray examination of the heart requiring simultaneous electrocardiographic recording.

While the preferred embodiment of the invention has been disclosed, it is understood that the invention is not limited to such an embodiment since it may be otherwise embodied in the scope of the appended claims.

What is claimed is:

1. A disposable radiotransparent electrode which presents a substantially invisible image in X-ray photographs comprising a foam container provided with an adhesive surface, a first well cut in the adhesive surface of said foam container, a layered conductive structure mounted in said first well, said layered conductive structure comprising a plastic base and a gold metallic film layer deposited thereon of about 3,000 angstroms in thickness, an insulated wire with one end connected to said gold metallic film layer and the other end extending from said foam container, an electrical connector assembly, the other end of said insulated wire being secured to said electrical connector assembly, said insulated wire being constructed of an electrically conductive material and having a thickness not exceeding 36 AWG allowing it to be radiotransparent, a mounting board mounted to said adhesive surface, said mounting board defining a second well, a sponge received in said second well, said sponge projecting into said first well and engaging the gold metallic film layer of said layered conductive structure and electrode gel located in the well of the mounting board.

2. An electrode as claimed in claim 1 wherein said insulated wire comprises a copper strand with a thickness of about 36 AWG.

3. An electrode as claimed in claim 1 wherein said container comprises a latex foam structure having an adhesive surface on at least one side.

4. An electrode as claimed in claim 3 wherein said latex foam structure is circular in shape and defines a substantially circular well therein.

5. An electrode as claimed in claim 1 wherein said layered conductive structure comprises a substantially circular central portion and a tang portion extending therefrom.

6. An electrode as claimed in claim 1 wherein said gold metallic film layer is vacuum deposited and said plastic base is mylar about 2 mils in thickness.

7. A disposable radiotransparent electrode which presents a substantially invisible image in X-ray photographs comprising a foam container provided with an adhesive surface, a first well cut in the adhesive surface of said foam container, a layered conductive structure mounted in said first well, said layered conductive structure comprising a flexible paper base and a gold metallic film layer deposited thereon of about 3,000 angstroms in thickness, an insulated wire with one end connected to said gold metallic film layer and the other end extending from said foam container, an electrical connector assembly, the other end of said insulated wire being secured to said electrical connector assembly, said insulated wire being constructed of an electrically conductive material and having a thickness not exceeding 36 AWG allowing it to be radiotransparent, a mounting board mounted to said adhesive surface, said mounting board defining a second well, a sponge received in said second well, said sponge projecting into said first well and engaging the gold metallic film layer of said layered conductive structure and electrode gel located in the well of the mounting board.

* * * * *